(12) United States Patent
Hart et al.

(10) Patent No.: US 6,520,937 B2
(45) Date of Patent: Feb. 18, 2003

(54) FLUID INJECTION DEVICE

(75) Inventors: Colin P. Hart, Queensbury, NY (US); Robert L. Barry, Kirkland, WA (US); Theodore C. Lamson, Pleasanton, CA (US); Gregory H. Lambrecht, Natick, MA (US); Brett Stern, New York, NY (US)

(73) Assignee: SciMed Life Systems, Inc., Maple Grove, MN (US)

( * ) Notice: Subject to any disclaimer, the term of this patent is extended or adjusted under 35 U.S.C. 154(b) by 88 days.

(21) Appl. No.: 09/739,403

(22) Filed: Dec. 18, 2000

(65) Prior Publication Data

US 2002/0077597 A1 Jun. 20, 2002

(51) Int. Cl.$^7$ ................................................ A61M 1/00
(52) U.S. Cl. .................. 604/151; 604/30; 604/132; 604/247; 604/99.02
(58) Field of Search .............................. 604/30, 33, 34, 604/132, 142, 143, 153, 183, 184, 185, 204, 212, 213, 214, 246, 247, 250, 96.01, 22, 35, 18, 99.02, 151; 417/478

(56) References Cited

U.S. PATENT DOCUMENTS

| | | | |
|---|---|---|---|
| 2,866,457 A | 12/1958 | Moore | 128/214 |
| 2,999,499 A | 9/1961 | Willet | 128/214 |
| 3,001,525 A | 9/1961 | Hendricks | 128/214 |
| 3,057,350 A | 10/1962 | Cowley | 128/214 |
| 3,211,150 A | 10/1965 | Foderick | 128/349 |
| 3,533,400 A | 10/1970 | Palich | 128/2.05 |
| 3,776,229 A | 12/1973 | McPhee | 128/214 C |
| 3,951,145 A | 4/1976 | Smith | 128/214 R |
| 4,038,983 A | 8/1977 | Mittleman et al. | |
| 4,078,563 A | 3/1978 | Tuseth | 128/214 C |
| 4,175,558 A | 11/1979 | Hess, III et al. | 128/214 C |
| 4,325,368 A | 4/1982 | Kaemmerer | 128/214 R |
| 4,425,123 A | 1/1984 | Di Salvo | 604/247 |
| 4,428,383 A | 1/1984 | DeVroom | 128/748 |
| 4,534,757 A | 8/1985 | Geller | 604/85 |
| 4,548,598 A | 10/1985 | Theeuwes | 604/85 |
| 4,734,091 A | 3/1988 | Boyle et al. | 604/54 |
| 4,750,643 A | 6/1988 | Wortrich | 222/81 |
| 4,858,619 A | 8/1989 | Toth | 128/748 |
| 4,869,457 A | 9/1989 | Ewerlöf | 251/6 |
| 4,892,524 A | 1/1990 | Smith | 604/246 |
| 4,976,685 A | 12/1990 | Block, Jr. | 604/52 |
| 5,059,173 A | 10/1991 | Sacco | 604/80 |
| 5,074,334 A | 12/1991 | Onodera | 137/625.41 |
| 5,078,688 A | 1/1992 | Lobodzinski et al. | 604/164 |
| 5,084,031 A | 1/1992 | Todd et al. | 604/248 |
| 5,135,026 A | 8/1992 | Manska | 137/555 |
| 5,167,643 A | 12/1992 | Lynn | 604/263 |
| 5,238,026 A | 8/1993 | Goto | 138/30 |
| 5,334,170 A | * 8/1994 | Moroski | 604/80 |
| 5,356,375 A | * 10/1994 | Higley | 604/52 |
| 5,423,751 A | 6/1995 | Harrison et al. | 604/83 |
| 5,533,978 A | 7/1996 | Teirstein | 604/183 |
| 5,569,208 A | * 10/1996 | Woelpper et al. | 604/183 |
| 5,593,385 A | 1/1997 | Harrison et al. | 604/83 |

(List continued on next page.)

FOREIGN PATENT DOCUMENTS

EP 0 413 069 A1 2/1991

Primary Examiner—Charles G. Freay
Assistant Examiner—Han L Liu
(74) Attorney, Agent, or Firm—Crompton, Seager & Tufte, LLC

(57) ABSTRACT

A catheter for use in vasculature or other body lumen includes a fluid injection bypass tube, leading to a elastically compressible pump bulb. Upon compression of the pump bulb, fluid such as contrast solution is injected through a one-way valve, into the catheter manifold lumen, and ultimately to the distal end of the catheter lumen, and into the patient vasculature. The one-way valve between the pump bulb and the catheter lumen has a threshold pressure to prevent unintended aspiration of fluid from the pump bulb during aspiration of fluid from the catheter itself.

36 Claims, 3 Drawing Sheets

U.S. PATENT DOCUMENTS

| | | |
|---|---|---|
| 5,665,074 A | 9/1997 | Kelly .................... 604/247 |
| 5,743,872 A | 4/1998 | Kelly .................... 604/49 |
| 5,779,666 A * | 7/1998 | Teristein .................. 604/52 |
| 5,807,321 A * | 9/1998 | Stoker et al. ............ 604/65 |
| 5,911,708 A | 6/1999 | Teirstein |
| 6,056,727 A | 5/2000 | O'Neil |
| 6,063,052 A | 5/2000 | Uber, III et al. |
| 6,371,942 B1 * | 4/2002 | Schwartz et al. ......... 604/246 |

* cited by examiner

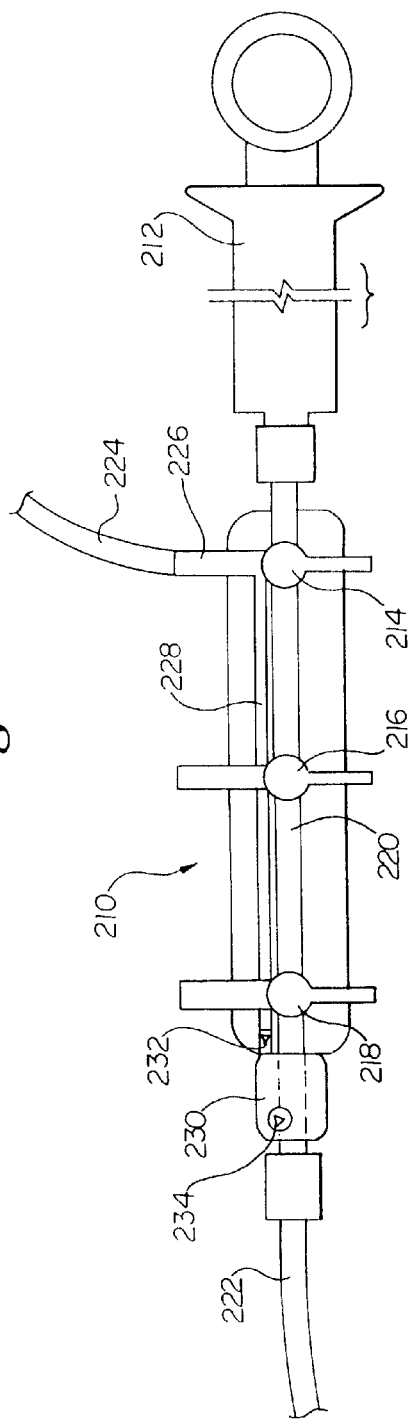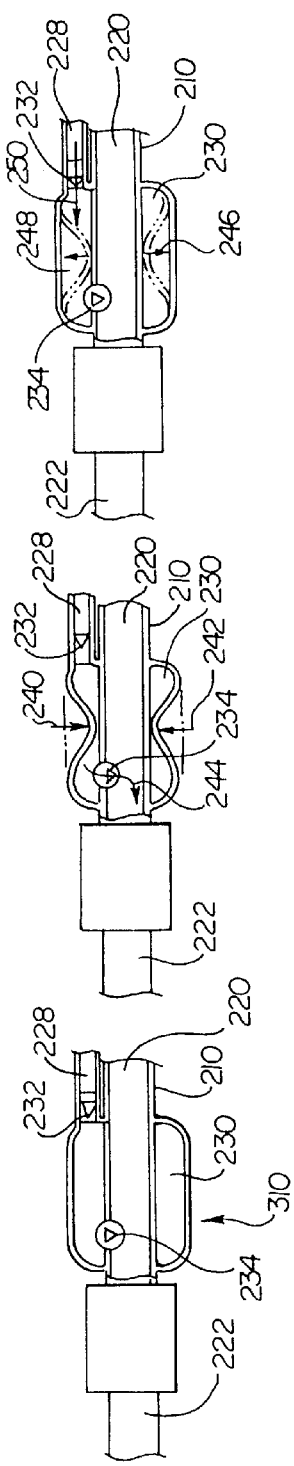

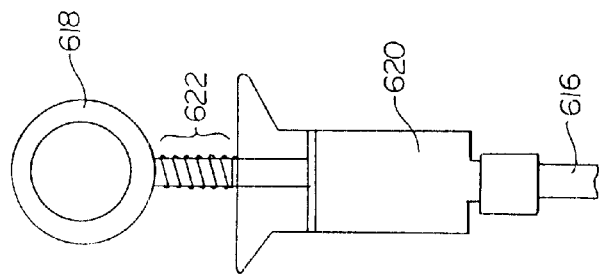
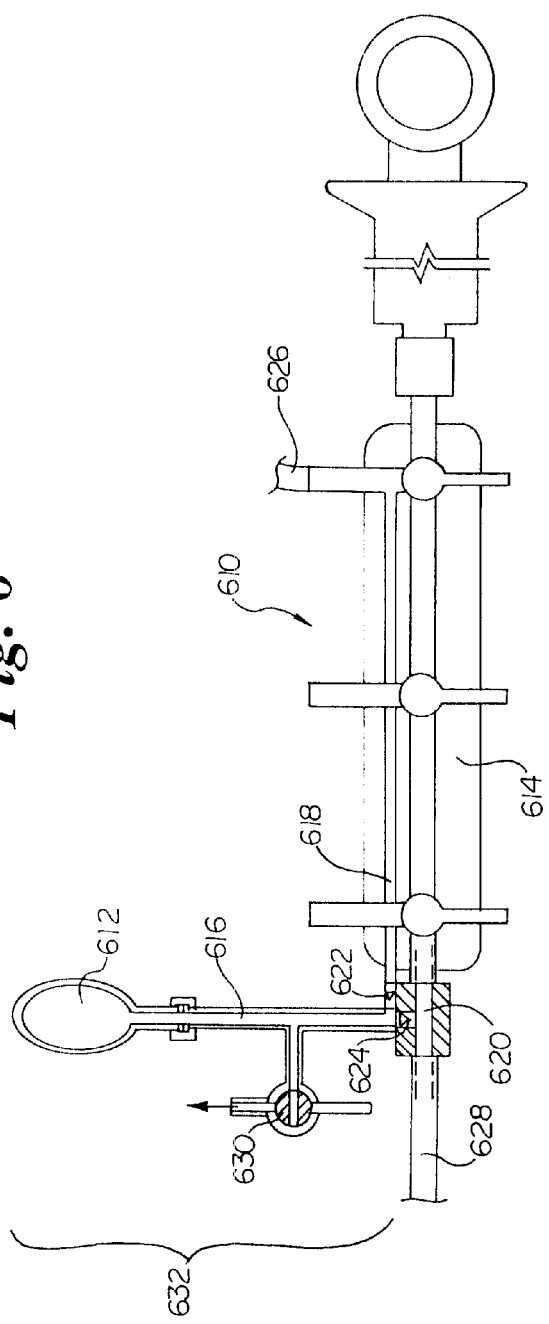

FLUID INJECTION DEVICE

FIELD OF THE INVENTION

The present invention relates to the field of catheterization of a lumen within the human body, particularly the vasculature. Even more particularly, the invention will have application to the manufacture and construction of balloon catheters used in angioplasty.

BACKGROUND OF THE INVENTION

Angioplasty procedures have gained wide acceptance as an efficient and effective method for treating certain types of vascular disease. In particular, angioplasty is widely used for stenoses in the coronary arteries, although it is also used for the treatment of stenoses in other parts of the vascular system.

The most widely used form of angioplasty makes use of a dilatation balloon catheter to treat a stenosis and thereby reestablish an acceptable blood flow through the artery. The dilatation catheter includes an elongated tubular shaft and an inflatable balloon carried at a distal end of the shaft. In operation, the catheter is inserted through a guide catheter which has been previously introduced into a patient's vascular system from a location remote from the heart (e.g., femoral artery). The proximal end of the guide catheter remains outside the patient, while the distal end of the guide catheter is positioned at the coronary artery ostium. A dilatation catheter is introduced into the proximal end of the guiding catheter and advanced to the distal end of the guide catheter. Then, by using fluoroscopy, the physician guides the dilatation catheter the remaining distance through the vascular system until the balloon is positioned across the stenosis.

Fluoroscopy, the use of radiographic images to view a catheter's position and progress through a patient's vasculature, is essential in allowing the interventional radiologist to accomplish the desired results during diagnostic procedures such as angiography and treatment procedures such as angioplasty. Catheters are made visible through the use, for example, of radiopaque materials impregnated in the catheter materials, or radiopaque marker bands around the catheters. Radiopaque contrast solution, when injected into patient vasculature at the distal end of the catheter, permits the physician to see otherwise virtually invisible vasculature and chart out the desired course of the catheter being guided to the diagnostic or treatment site. Accordingly, the simple and safe injection of contrast media is a basic necessity for all angiographic procedures. Virtually every case of angiographic and other interventional radiological intervention requires multiple contrast injections to visualize the patient's peripheral vasculature, coronary vessels, bypass grafts, or other treatment site vasculature.

The typical practice of physicians in delivering contrast media is to hand inject contrast media down the lumen of a catheter using a syringe connected to an angiographic manifold. The hand injection process requires the physician to manipulate at least one, if not multiple, stopcock valves on the manifold to allow them to aspirate contrast into the syringe and then inject it into the patient. Because of the multiple stopcocks and syringes that must be manipulated, the procedure requires two hands and typically about nine separate steps to perform. This procedure is cumbersome and time consuming. In addition, the inconvenience of existing methods of delivery may force the physician's attention away from the catheter which is being steered through the patient vasculature.

SUMMARY OF THE INVENTION

The present invention reduces the hand injection of contrast to one simple step, the squeeze of a small pump located on or near the manifold. Because of its ease of operation, a device of the instant invention can be used to inject contrast during the placement of a catheter, providing the additional benefit of real-time assessment of catheter position as it is manipulated. Former methods of contrast fluid introduction were often too unwieldy to permit their use during catheter placement.

The present invention provides a parallel or alternate route for the injection of a fluid bolus, such as contrast solution, into a catheter during catheter placement, or during other aspects of interventional radiographic treatment or diagnosis. The former turning of various stopcocks or valves is replaced with the relatively simple squeeze of a pump bulb, which injects a bolus of the desired fluid into the catheter lumen. If more fluid is desired, the physician may simply make quick repeated injections of fluid in addition to that already injected.

The fluid inlet of an embodiment of the present invention is hooked up not only to the typical stopcocks of a manifold, but in addition to a fluid bypass tube running to a small pump. In a preferred embodiment, this pump is manually operated for simple and precise use. In one embodiment of the subject invention described below, the pump takes the form of a squeezable bulb that will eject fluid when squeezed, and when released, springs back into its original shape, drawing more fluid from the fluid source.

In a preferred embodiment, the outlet valve of the pump bulb, in addition to having the property of being a one-way valve, also has a cracking or threshold pressure. This cracking pressure is the pressure gradient between the supply side of the valve to the destination side of the valve, below which the valve will not allow flow through the valve. In other words, the pressure on the supply side of the valve must exceed the pressure on the destination side of the valve by an amount at least equal to the cracking pressure before the valve allows any fluid to flow through it. The use of a valve with a cracking pressure at the outlet valve of the pump bulb is preferred because this prevents the exit of contrast media from the pump bulb when the physician is aspirating fluid from the catheter lumen. If a valve without a cracking pressure was used, the pressure gradient created by the aspiration of the lumen would tend to suck contrast fluid at least in part from the pump bulb, rather than entirely from the catheter lumen as is intended. As long as the pressure gradient created by the aspiration of the catheter lumen is less than the cracking pressure of the outlet valve, the aspiration will not cause contrast fluid to escape from the pump bulb. Therefore, in a preferred embodiment, the cracking pressure of the pump bulb outlet valve is greater than the pressure gradient between the pump bulb and the catheter lumen caused by aspiration of the catheter lumen with a syringe.

One embodiment of the present invention has a pump bulb that ejects approximately 2 ml of contrast media with each complete squeeze of the pump bulb. Because the bulb cannot be completely evacuated by the squeeze administered by the operator, a preferred embodiment of the invention will have a pump bulb volume in excess of 2 ml. In an alternate embodiment of the present invention, the pump reservoir is a type of modified syringe, i.e., a cylindrical tube with a plunger for ejecting the fluid into the catheter shaft. In this embodiment, the pump reservoir has a compression spring that tends to push the plunger out of the reservoir to increase the volume of fluid in the syringe. The syringe style of pump reservoir may have volume indicator lines embossed or printed on the syringe and be transparent or translucent so that the volume of fluid in the reservoir may be viewed. This embodiment may be preferred for applications where more precise measurement of the volume of fluid injected into the catheter or tube is necessary, for example, if the invention is used to deliver therapeutic agents as opposed to contrast solution.

One embodiment of the present invention is a catheter in which a fluid injector or pump is an integral component of a catheter manifold. The present invention, however, may also be implemented as an auxiliary or add-on device which may be used with a variety of medical devices. For example, an embodiment of the instant invention may be used with any catheter that a physician prefers or finds most suitable for a particular application. The instant invention, when embodied in an add-on unit, may also be built with devices such as syringes, intravascular lines, and other devices using tubular conduit.

The use of a one-way valve at the pump bulb inlet and outlet valves are necessary because after the pump ball is squeezed to force fluid into the catheter lumen, and the pump bulb begins to expand again, the fluid that will fill the pump bulb must be supplied from the fluid supply vessel, and not from the delivery conduit leading to the catheter. If the fluid was allowed to flow back into the pump bulb, the fluid just delivered would be immediately aspirated back out of the catheter lumen by the low pressure created by the elastic expansion of the pump bulb. This, in turn, would cause fluid to be sucked into the catheter from the patient's bloodstream. Of course, when the pump bulb was squeezed again, the contrast media or other fluid would not be delivered as expected at the catheter's distal end.

BRIEF DESCRIPTION OF THE DRAWINGS

FIG. 2 is a plan view of an embodiment of the present invention integrated into a specially designed manifold;

FIG. 3 is a cross-sectional view of the pump reservoir of the catheter manifold of FIG. 2;

FIG. 4 is a cross-sectional view of the pump reservoir of FIG. 3, showing the flow of contrast media upon compression;

FIG. 5 is a cross-sectional view of the pump reservoir of FIGS. 3 and 4, showing the flow of contrast media upon elastic expansion of the pump reservoir after compression ceases;

FIG. 6 is a plan view of an alternate embodiment of the present invention with a side pump;

FIG. 7 is a plan view of an alternate embodiment of the fluid ejector for the pump shown in FIG. 6.

DETAILED DESCRIPTION OF THE DRAWINGS

Figure 1:
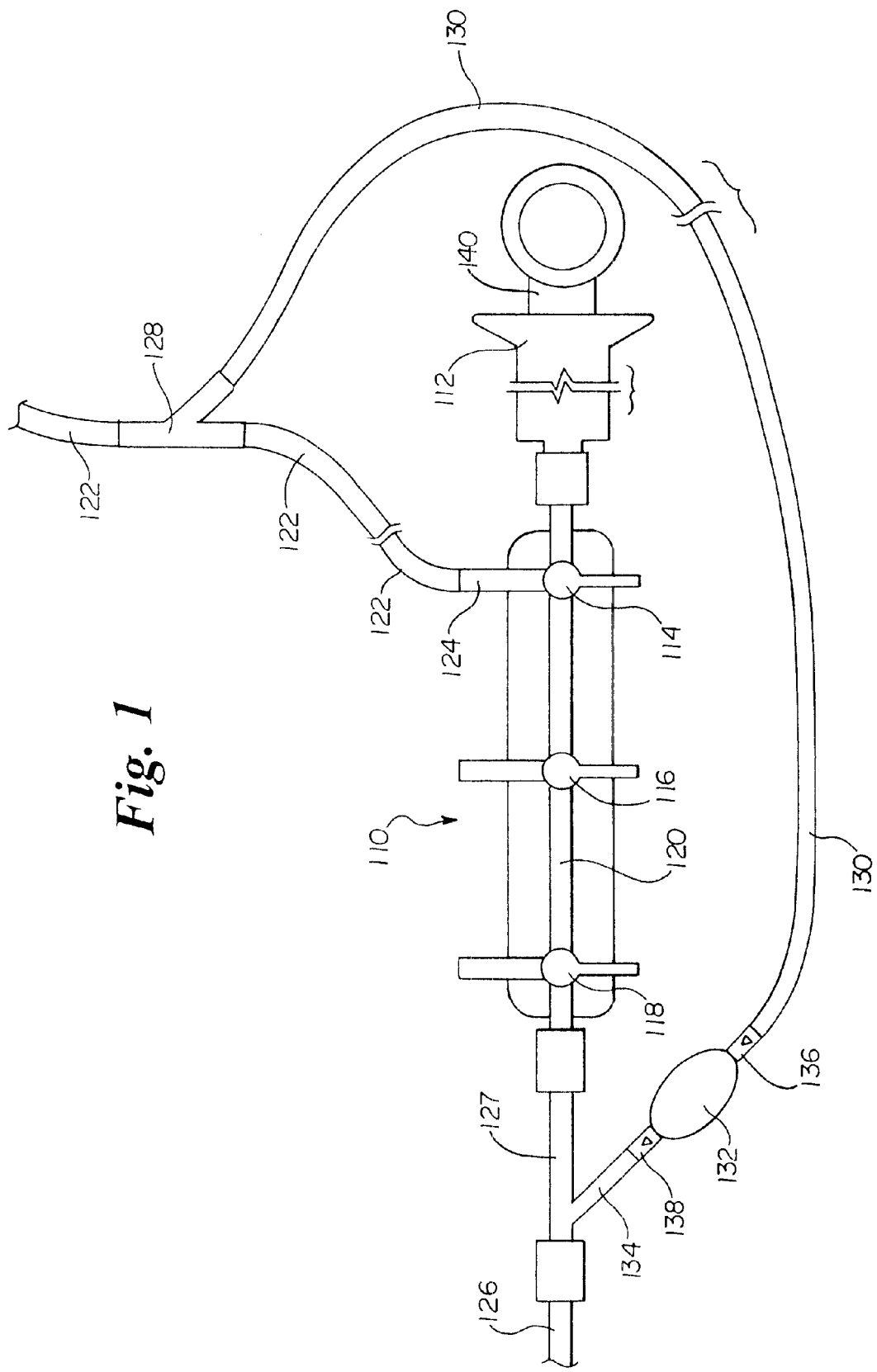
FIG. 1 is a plan view of an embodiment of the present invention adapted for use with existing catheter manifold designs.

In FIG. 1, an embodiment of the present invention is shown by which the present invention may be used with a preexisting manifold preferred by the physician. This embodiment may be utilized with an angiographic manifold or other appropriate catheter manifold. The preexisting catheter manifold is shown generally at 110. The manifold consists of a syringe 112, stopcock valves 114, 116, and 118, and a central lumen 120. A fluid feed line 122 enters the manifold at fluid line fitting 124. The fluid feed line 122 runs to a fluid bottle, not depicted, such as a bottle of radiographic contrast solution containing a radiopaque substance. The manifold 110 is fitted to a suitable catheter 126, through Y-fitting 127.

The embodiment of the subject invention is fitted to the existing manifold 110 by a Y-connection or bifurcated spike 128. The bifurcated spike 128 is fitted to the fluid feed line 122 as well as the fluid inlet conduit 130 of this embodiment of the present invention. The fluid inlet conduit 130 connects to an elastically compressible reservoir pump 132. Upon compression, fluid in the compressible reservoir pump 132 is forced from the reservoir 132 into pump outlet tube 134. Fluid is not forced from reservoir pump 132 into the fluid inlet conduit 130, because one-way valve 136 allows fluid to flow only in the distal direction, as indicated by the arrow on the valve 136.

After the reservoir 132 is released, it expands to its previous uncompressed shape, as depicted. Fluid then flows from fluid inlet conduit 130 into reservoir pump 132. Fluid is not drawn from pump outlet tube 134 and into the reservoir 132, because one-way valve 138 prevents flow in this direction, only allowing flow in the distal direction as indicated by the arrow on valve 138. Pump outlet tube 134, part of Y-fitting 127, joins catheter 126, and thus fluid expelled out of reservoir 132 will enter the lumen of catheter 126.

In a preferred embodiment of the present invention, one-way valve 138 has a threshold, or "cracking" pressure, required to produce flow of fluid through one-way valve 138. This prevents aspiration of fluid from the reservoir 132 when fluid is aspirated from the manifold lumen 120, for example, by withdrawal of the syringe plunger 140 from syringe 112. Without a cracking pressure, when a physician wants to take a sample of fluid from the manifold lumen 120, the low pressure caused by the aspiration would draw fluid from reservoir 132 into manifold lumen 120, just as it would if the reservoir 132 were compressed. This undesirable effect is prevented by the use of a one-way valve 138 with a threshold opening pressure.

FIG. 2 shows an alternate embodiment of the current invention in which the present invention is integrated into a catheter manifold, such as an angiographic manifold. A manifold of this embodiment is shown generally at 210. The manifold has a syringe 212, as well as stopcock valves 214, 216, and 218. The manifold has a central lumen 220 in fluid communication with the central lumen of a catheter 222 fitted to the manifold 210. In this embodiment of the present invention, a fluid feed line 224 runs to a fluid bottle, which is not depicted. The fluid feed line 224 is fitted to manifold fluid fitting 226, and the fluid from the feed line may be introduced into manifold lumen 220 by the use of stopcock valve 214. The manifold fluid fitting 226 also is in fluid communication with a fluid bypass tube 228, an embodiment of the fluid inlet conduit of the present invention. This fluid inlet conduit 228 leads to a compressible reservoir 230, which surrounds the distal end of the manifold 210.

Upon compression by the physician, fluid in the reservoir 230, such as contrast media, is forced through one-way valve 234 into manifold lumen 220, from which point it is further delivered through catheter 222 to a distal portion of catheter 222 (not depicted). Similar to the catheter of FIG. 1, one-way valve 232 keeps fluid from flowing from the reservoir 230 back to the fluid inlet conduit 228 when the reservoir is compressed. When the reservoir 230 expands upon cessation of compression, fluid may pass from fluid inlet conduit 228 through one-way valve 232. Fluid is not drawn from the manifold lumen 220 into reservoir 230 because one-way valve 234 prevents fluid from flowing back into the reservoir 230. As with the catheter of FIG. 1, in a preferred embodiment of the present invention, one-way valve 234 has a threshold, or 'cracking' pressure, to prevent fluid flow from the reservoir 230 into the manifold lumen 220 when fluids are aspirated from manifold lumen 220. The compression of the reservoir 230 is shown in detail in FIGS. 3 through 5.

FIG. 3 shows a cross-sectional view of an elastically compressible pump reservoir of an embodiment of the present invention, that shown in FIG. 2. The reservoir 230, in a preferred embodiment of the subject invention, is made of a flexible polymeric material, and may be made of a translucent material so that the existence of fluid in the reservoir may be confirmed. The reservoir is shown generally at 310. Catheter 222 is fitted to manifold 210. Therefore, manifold lumen 220 is in fluid communication with the lumen of catheter 222. The compressible reservoir 230 is filled with fluid, such as radiographic contrast fluid, which has previously entered the reservoir 230 from the fluid inlet conduit 228. The reservoir 230 is in a stable state, and no fluid is flowing through the one-way valves 232 and 234. One-way valve 234, in a preferred embodiment, has a threshold pressure that is required before fluid flow will commence out of reservoir 230 and into manifold lumen 220. This feature will tend to prevent aspiration of fluid from reservoir 230 if fluid is aspirated from manifold lumen 220.

FIG. 4 shows the compressible reservoir 230 of FIG. 3, the reservoir 230 undergoing compression by the physician. The forces applied by the physician are shown by arrows 240 and 242. This force results in compression of the flexible reservoir 230, as shown. During the compression, preferably no fluid flows from fluid inlet conduit 228 through one-way valve 228. The flow of fluid during compression is shown by arrow 244.

FIG. 5 shows a cross-section of the compressible reservoir 230 of FIGS. 3 and 4. Upon cessation of compression of the elastically compressible reservoir 230, the reservoir 230 automatically reverts to its former uncompressed shape, due to the elastomeric properties of the polymeric material used for the reservoir 230. Suitable materials for the reservoir 230 are silicone, rubber or other polymeric material. Lines 246 and 248 indicate the movement of the outside walls of reservoir 230 following the release of pressure from forces 240 and 242 in FIG. 4. The reduction in pressure within reservoir 230 causes fluid to be sucked out of the fluid inlet conduit 228, through one-way valve 232. The fluid flow is indicated by arrow 250. In a preferred embodiment of the present invention, no fluid moves through the one-way valve 234.

FIG. 6 shows a plan view of an alternate embodiment of the present invention, shown generally at 610, in which the reservoir fluid ejector 612 is adapted to project from the side of the manifold 614. An elongate reservoir tube 616 connects the reservoir fluid ejector 612 to the fluid inlet conduit 618 and the manifold lumen 620.

One-way valves 622 and 624, disposed along reservoir tube 616, prevent fluid from flowing except in the intended direction. The fluid ejector 612, reservoir tube 616, and one-way valves 622 and 624 together form the pump means 632 of this embodiment of the present invention. Fluid is ultimately supplied from a fluid source, not depicted, such as a contrast solution bottle connected to fluid feed line 626. The fluid enters the catheter through fluid feed line 626. In this embodiment, fluid is dispensed by compression of the fluid ejector 612, forcing fluid through reservoir tube 616, through manifold lumen 620, and ultimately into catheter 628 and to the distal end of the catheter, not depicted. When the fluid ejector bulb 612 is released, it returns to its former shape, drawing fluid through one-way valve 622. The bulb-type fluid ejector 612 may be replaced by a spring-loaded syringe, as shown in FIG. 7.

As shown in FIG. 6, in a preferred embodiment of the subject invention, debubbling valve 630 is provided, which may be opened so as to allow air bubbles that might collect in the reservoir 612 or in the elongate reservoir tube 616, either during setup of the apparatus, or during the procedure if air or other gas bubbles form or are introduced. The gas bubbles may be forced out of the reservoir tube through open valve 630, aided by compression of the reservoir 612. This aids in preventing the introduction of gas bubbles into the vasculature of the patient, gas bubbles being an undesired effect. Generally, in a preferred embodiment of the subject invention, a debubbling valve is utilized by placing the debubbling valve within or in fluid communication with the pump or reservoir element of the invention, between the inlet port and outlet port of the pump element of the invention.

FIG. 7 shows a plan view of a syringe-style fluid ejector or pump of an embodiment of the present invention that may be used in place of bulb-style fluid ejector 612 in FIG. 6. In this embodiment of the present invention, fluid is ejected out of the elongate reservoir tube 616 by compression of syringe plunger 618. When plunger 618 is released, it is forced back out of the syringe body 620 by compression spring 622. This retraction of the syringe plunger 618 creates the suction that draws fluid out of fluid inlet conduit 618, through one-way valve 622, not shown in FIG. 7, and into reservoir tube 616 and syringe body 620.

Although the present invention has been described with reference to preferred embodiments, workers skilled in the art will recognize that changes may be made in form and detail without departing from the spirit and scope of the invention.

What is claimed is:

1. A fluid injection device for use with an intravascular catheter, the catheter having a proximal portion, a distal portion, and a lumen extending therethrough, the fluid injection device comprising;

a manifold disposed at the proximal portion of the catheter;

a fluid inlet conduit disposed at the proximal portion of the catheter, the inlet conduit having a proximal portion and distal portion, the proximal portion of the inlet conduit being in fluid communication with a fluid source, the distal portion of the conduit in fluid communication with the catheter lumen and disposed distally of the manifold;

means for injecting a bolus of fluid from the fluid inlet conduit into the catheter lumen operatively connected to said fluid inlet conduit; and means for preventing backflow of the fluid bolus.

2. The fluid injection device of claim 1, wherein the fluid inlet conduit is at least partially integrated into a catheter manifold.

3. The fluid injection device of claim 1, where in the means for injecting a bolus of fluid comprises a pump having an inlet port and an outlet port.

4. The fluid injection device of claim 3, wherein the means for injecting a bolus of fluid further comprises a pump outlet tube disposed between the outlet port of the pump and the catheter lumen, the outlet tube having a distal and proximal end, the outlet port of the pump being in fluid communication with the proximal end of the pump outlet tube, and the distal end of the pump outlet tube being in fluid communication with the catheter lumen.

5. The fluid injection device of claim 3, further comprising means for preventing backflow of fluid from the pump to the fluid inlet conduit.

6. The fluid injection device of claim 3, wherein the means for preventing backflow of the fluid bolus comprises a first one-way valve disposed proximate to the pump outlet port.

7. The fluid injection device of claim 6, wherein the means for preventing backflow of fluid from the pump to the fluid inlet conduit comprises a second one-way valve disposed proximate to the pump inlet port.

8. The fluid injection device of claim 3, wherein the pump comprises an elastically compressible reservoir.

9. The fluid injection device of claim 8, wherein the elastically compressible reservoir is aligned with the fluid inlet conduit.

10. The fluid injection device of claim 8, where the reservoir has a volume between 1 and 5 ml.

11. The fluid injection device of claim 8, where the reservoir is made of a polymeric material.

12. The fluid injection device of claim 11, where the reservoir is made from a translucent or transparent material.

13. The fluid injection device of claim 3, further including a debubbling valve disposed between the inlet port and outlet port, in fluid communication with the pump.

14. The fluid injection device of claim 3, wherein the pump comprises an elongate reservoir tube in fluid communication with a fluid expulsion means, the inlet port and outlet ports of the pump being disposed along the elongate reservoir tube.

15. The fluid injection device of claim 14, wherein a one-way valve is disposed proximate to each of the inlet port and outlet ports.

16. The fluid injection device of claim 14, wherein the fluid expulsion means comprises an elastically compressible reservoir.

17. The fluid injection device of claim 14, wherein the fluid expulsion means comprises a spring-loaded syringe.

18. The fluid injection device of claim 1, wherein the means for injecting a bolus of fluid comprises a pump disposed at the distal portion of the fluid inlet conduit, the pump having an inlet port and an outlet port, the inlet port being in fluid communication with the fluid inlet conduit, the outlet port being in fluid communication with the catheter lumen.

19. The fluid injection device of claim 18, wherein the pump disposed at the distal portion of the fluid inlet conduit comprises an elastically compressible reservoir.

20. The fluid injection device of claim 19, wherein the elastically compressible reservoir is aligned with the fluid inlet conduit.

21. The fluid injection device of claim 19, wherein the means for preventing backflow of the fluid bolus comprises a one-way valve disposed proximate to the pump outlet port.

22. The fluid injection device of claim 1, further comprising means for preventing the aspiration of fluid from the bolus injecting means into the catheter lumen when fluid is being aspirated from the catheter lumen.

23. The fluid injection device of claim 22, wherein the means for preventing the aspiration of fluid from the bolus injecting means into the catheter lumen comprises a one-way valve disposed between the pump outlet port and the catheter lumen, the one-way valve having a threshold pressure gradient required for flow that is greater than the pressure gradient created by aspiration of fluid from the catheter lumen.

24. An intravascular catheter comprising:
an elongate tubular body having a proximal portion, a distal portion, and a catheter lumen extending therethrough;
a fluid inlet conduit disposed at the proximal portion of the tubular body, the inlet conduit having a proximal portion and distal portion, the proximal portion of the inlet conduit being in fluid communication with a fluid source, the distal portion of the inlet conduit in fluid communication with the catheter lumen;
a pump for injecting a bolus of fluid from the fluid inlet conduit into the catheter lumen; and
a one-way valve in the distal portion of the inlet fluid conduit for preventing backflow of the fluid bolus from the catheter lumen.

25. The intravascular catheter of claim 24, wherein the fluid inlet conduit is at least partially integrated into a catheter manifold.

26. The intravascular catheter of claim 24, wherein the pump includes a pump outlet tube disposed between the outlet port of the pump and the catheter lumen, the outlet tube having a distal and proximal end, the outlet port of the pump being in fluid communication with the proximal end of the pump outlet tube, and the distal end of the pump outlet tube being in fluid communication with the catheter lumen.

27. The intravascular catheter of claim 24, further comprising a second one-way valve in the proximal portion of the fluid inlet conduit for preventing backflow of fluid from the pump to the fluid inlet conduit.

28. The intravascular catheter of claim 24, wherein the pump comprises an elastically compressible reservoir.

29. The intravascular catheter of claim 28, wherein the elastically compressible reservoir is aligned with the tubular body.

30. The intravascular catheter of claim 28, where the reservoir has a volume between 1 and 5 ml.

31. The intravascular catheter of claim 28, where the reservoir is made of a polymeric material.

32. The intravascular catheter of claim 31, where the reservoir is made from a translucent or transparent material.

33. The intravascular catheter of claim 24, wherein the pump comprises an elongate reservoir tube in fluid communication with a fluid expulsion means, the inlet port and outlet ports of the pump being disposed along the elongate reservoir tube.

34. The intravascular catheter of claim 33, wherein a one-way valve is disposed proximate to each of the inlet port and outlet ports.

35. An intravascular catheter comprising:
an elongate tubular body having a proximal portion, a distal portion, and a catheter lumen extending therethrough; and
a manifold having a proximal and distal end, disposed proximally of the proximal portion of the tubular body, the manifold comprising:
an elongate tubular body having an exterior wall, with a manifold lumen extending therethrough, the manifold lumen having an interior wall;
a proximal opening at the proximal end of the manifold, the proximal opening being in fluid communication with the manifold lumen;
a distal opening at the distal end of the manifold, the distal opening being in fluid communication with both the manifold lumen and with the catheter lumen;
a fluid input opening disposed in the exterior wall of the manifold, the fluid opening accepting a contrast solution supply line;
a fluid bypass lumen disposed between the exterior wall of the manifold and the interior wall of the manifold lumen, the fluid bypass lumen being in fluid communication with the fluid input opening;

an elastically compressible pump reservoir having an interior, an exterior, an inlet port, and an outlet port, the inlet port being in fluid communication with the fluid bypass lumen, and the outlet port being in fluid communication with the catheter lumen;

a one-way inlet valve disposed adjacent the pump reservoir inlet port, and being disposed so as to not allow fluid to flow from the pump reservoir to the fluid bypass lumen; and a one-way outlet valve, disposed adjacent the pump reservoir outlet port, and being disposed so as to not allow fluid to flow from the catheter lumen to the pump reservoir.

36. The intravascular catheter of claim 35, further comprising a debubbling valve disposed between the inlet valve and outlet valve, the debubbling valve being in fluid communication with the pump reservoir.

* * * * *